US010640663B2

(12) United States Patent
Park

(10) Patent No.: US 10,640,663 B2
(45) Date of Patent: May 5, 2020

(54) CERAMIC PRINTING INK COMPOSITION HAVING ANTIBACTERIAL FUNCTION

(71) Applicant: THERMOLON KOREA CO.,LTD, Busan (KR)

(72) Inventor: Chung Kwon Park, Busan (KR)

(73) Assignee: THERMOLON KOREA CO., LTD., Busan (KR)

( * ) Notice: Subject to any disclaimer, the term of this patent is extended or adjusted under 35 U.S.C. 154(b) by 300 days.

(21) Appl. No.: 15/579,707

(22) PCT Filed: Jul. 26, 2016

(86) PCT No.: PCT/KR2016/008155
§ 371 (c)(1),
(2) Date: Dec. 5, 2017

(87) PCT Pub. No.: WO2017/018776
PCT Pub. Date: Feb. 2, 2017

(65) Prior Publication Data
US 2018/0163065 A1 Jun. 14, 2018

(30) Foreign Application Priority Data

Jul. 28, 2015 (KR) .................. 10-2015-0106673

(51) Int. Cl.
| | | |
|---|---|---|
| *C09K 3/00* | (2006.01) | |
| *C09D 11/033* | (2014.01) | |
| *C09D 11/037* | (2014.01) | |
| *C09D 5/14* | (2006.01) | |
| *C09D 7/40* | (2018.01) | |
| *B41M 5/00* | (2006.01) | |
| *C01B 33/12* | (2006.01) | |
| *C07C 31/10* | (2006.01) | |
| *C07C 31/20* | (2006.01) | |
| *C09D 1/00* | (2006.01) | |
| *C09D 4/00* | (2006.01) | |
| *C09D 5/00* | (2006.01) | |
| *C09D 11/00* | (2014.01) | |

(52) U.S. Cl.
CPC .......... *C09D 11/033* (2013.01); *B41M 5/007* (2013.01); *C01B 33/12* (2013.01); *C07C 31/10* (2013.01); *C07C 31/202* (2013.01); *C09D 5/14* (2013.01); *C09D 7/40* (2018.01); *C09D 11/037* (2013.01); *C01P 2004/12* (2013.01); *C01P 2006/16* (2013.01)

(58) Field of Classification Search
USPC ................................ 106/31.01, 31.05, 31.13
See application file for complete search history.

(56) References Cited

U.S. PATENT DOCUMENTS

| | | | | |
|---|---|---|---|---|
| 2014/0100329 A1* | 4/2014 | Clark | ................. | C08G 18/4887 |
| | | | | 524/590 |
| 2015/0275043 A1* | 10/2015 | Kikuchi | ............... | C09D 183/04 |
| | | | | 428/220 |

FOREIGN PATENT DOCUMENTS

| | | | | |
|---|---|---|---|---|
| JP | 08-337078 | A | 12/1996 | |
| JP | 08337078 | A * | 12/1996 | |
| JP | 09-263725 | A | 10/1997 | |
| JP | 09263725 | A * | 10/1997 | |
| KR | 10-0750604 | B1 | 8/2007 | |
| KR | 10-0999170 | B1 | 12/2010 | |
| KR | 100999170 | B1 * | 12/2010 | ............... C09D 7/70 |
| KR | 10-2011-0064293 | A | 6/2011 | |

* cited by examiner

*Primary Examiner* — James E McDonough
(74) *Attorney, Agent, or Firm* — John K. Park; Park Law Firm

(57) ABSTRACT

The present invention relates to a ceramic printing ink composition having antibacterial function, and more particularly to a ceramic printing ink composition which is prepared by mixing deionized water, propylene glycol, propylene glycol methyl ether acetate (PMA) solvent, propylene glycol methyl ether (PM) solvent, isopropyl alcohol (IPA), a dispersing agent, a pigment. In a process of printing a pattern using the ceramic printing ink composition, the pattern is printed between or on ceramic coating layers by pad, screen or stamp printing. More specifically, ceramic coating (sol-gel) layers (1-coat, 2-coat, 3-coat, etc.) are formed and set-to-touch, after which the ceramic printing ink composition is coated on the coating layer and heated and cured simultaneously with the coating layers. Thus, bonding and adhesive strength of the ceramic printing ink composition is enhanced to enable printing to be more stably and easily performed on the ceramic coating layer.

3 Claims, No Drawings

CERAMIC PRINTING INK COMPOSITION HAVING ANTIBACTERIAL FUNCTION

TECHNICAL FIELD

The present invention relates to a ceramic printing ink composition which enables a pattern to be stably and easily printed on a ceramic coating layer and has an antibacterial function.

BACKGROUND ART

In recent years, a ceramic coating layer is formed on a kitchen appliance such as a rice cooker or the like in order to impart functionality such as non-stick performance to the kitchen appliance. On the other hand, various kinds of patterns (e.g., a reference line for adjusting the water level of a rice cooker, etc.) are printed or engraved on the kitchen appliance.

However, it is typically difficult to print such patterns on the ceramic coating layer. For example, when the ceramic coating layer is formed and then liquid ink is printed before the formed ceramic coating layer is cured, the ink spreads to thereby obstruct the patterns from being clearly printed. In addition, when the ceramic coating layer is formed and then liquid ink is printed after the formed ceramic coating layer is cured, a problem occurs in that the printed patterns are peeled off from the ceramic coating layer due to a weak mutual stickiness between the ceramic coating layer cured at high temperature and the liquid ink.

Therefore, typically, the inner surface of the rice cooker is cut away and then patterns such as a reference line and the like are engraved thereon, leading to a complexity of the manufacturing process and an increase in the manufacturing cost.

In an attempt to solve the above problem, there has been proposed a kitchen appliance having a ceramic print layer and a method for forming a ceramic print as disclosed in Korean Patent Laid-Open Publication No. 10-2003-0080753. In the above patent publication, a ceramic coating layer is formed on the inner surface of the kitchen appliance including a metal main body, and then ceramic ink is printed thereon in a semi-cured state and completely cured at high temperature. However, this ceramic print forming method entails a problem in that it is merely a partial change in the manufacture process and the used ink itself is not suitable for the ceramic coating layer, and thus a pattern is not printed properly on the ceramic coating layer. Furthermore, as an interest is currently increasingly focusing on environment and hygiene, the consumption of various kinds of antibacterial kitchenware is increasing. Therefore, there is a need for an antibacterial function for such a ceramic printing ink composition.

DISCLOSURE OF INVENTION

Technical Problem

Accordingly, the present invention has been made in order to solve the above-described problems occurring in the prior art, and it is an object of the present invention is to provide a ceramic printing ink composition which is prepared by mixing deionized water, propylene glycol, propylene glycol methyl ether acetate (PMA) solvent, propylene glycol methyl ether (PM) solvent, isopropyl alcohol (IPA), a dispersing agent, a pigment, a rheology modifier, and an aqueous antibacterial composition so that pattern printing can be stably and easily performed on a ceramic coating layer.

Further, another object of the present invention is to provide a ceramic printing ink composition which comprises the aqueous antibacterial composition as disclosed in Korean Patent No. 10-0999170 which was previously filed by the applicant and registered so as to have antibacterial function.

Still another object of the present invention is to provide a ceramic printing ink composition which is used in a process of printing a pattern in which the pattern is printed between or on ceramic coating layers by pad, screen or stamp printing, more specifically, ceramic coating (sol-gel) layers (1-coat, 2-coat, 3-coat, etc.) are formed and set-to-touch, after which the ceramic printing ink composition is coated on the coating layer and heated and cured simultaneously with the coating layers so that bonding and adhesive strength of the ceramic printing ink composition is enhanced to enable pattern printing to be more stably and easily performed on the ceramic coating layer.

Technical Solution

To achieve the above objects, the present invention provides a ceramic printing ink composition having an antibacterial function, the composition comprising an aqueous antibacterial composition.

More specifically, the ceramic printing ink composition having an antibacterial function may preferably comprise 10 to 25 wt % of deionized water, 4 to 13 wt % of propylene glycol, 0.5 to 4 wt % of PMA solvent, 0.4 to 4 wt % of PM solvent, 2 to 5 wt % of IPA, 0.1 to 2 wt % of a dispersing agent, 15 to 35 wt % of a pigment, 5 to 65 wt % of a rheology modifier, and 3 to 7 wt % of the aqueous antibacterial composition.

In the meantime, in the ceramic printing ink composition having an antibacterial function, the aqueous antibacterial composition may preferably be prepared by adding and dispersing 45 to 55 parts by weight of silica nanotubes, 30 to 40 parts by weight of a wetting/dispersing agent, 30 to 40 parts by weight of a co-solvent, and 4 to 6 parts by weight of an antifoaming agent in 100 parts by weight of deionized water, and the silica nanotubes may preferably contain 20000 to 100000 ppm of silver nanoparticles.

In addition, in the ceramic printing ink composition having an antibacterial function, the silica nanotubes may preferably include fine pores having a size of 30 to 50 nm, and have an overall length of 1 to 30 μm.

Advantageous Effects

The present invention has the following effects. A coating binder is absorbed during a printing/drying/curing process to achieve a bonding strength of the ink itself and a firm bonding between the ink and the ceramic coating layer. In addition, the ceramic printing ink composition of the present invention possesses an antibacterial function by using the aqueous antibacterial composition such that the overall composition can have a good miscibility so as not to hinder the antibacterial function of the aqueous antibacterial composition. Further, the ceramic printing ink composition of the present invention can implement a good wettability with respect to the ceramic coating layer through the adjustment of the surface tension, and have flowability and drying property that are suitable for ensuring workability of pad, screen or stamp printing and storage stability. Moreover, the ceramic printing ink composition of the present invention can be printed on the ceramic coating layer, particularly a sol-gel nonstick coating layer, and can minimize the effect of the coating layer on a change in the physical properties at the printing site by ensuring good adhesion properties and selecting of the constituent components.

BEST MODE FOR CARRYING OUT THE INVENTION

The present invention is directed to a ceramic printing ink composition having an antibacterial function. It is to be noted that only portions necessary for understanding the technical constitution of the present invention will be described and the description of the remaining portions will be omitted to avoid obscuring the subject matter of the present invention.

The ceramic printing ink composition having an antibacterial function according to the present invention will be described hereinafter in detail.

The ceramic printing ink composition having an antibacterial function of the present invention comprises 10 to 25 wt % of deionized water, 4 to 13 wt % of propylene glycol, 0.5 to 4 wt % of propylene glycol methyl ether acetate (PMA) solvent, 0.4 to 4 wt % of propylene glycol methyl ether (PM) solvent, 2 to 5 wt % of isopropyl alcohol (IPA), 0.1 to 2 wt % of a dispersing agent, 15 to 35 wt % of a pigment, 5 to 65 wt % of a rheology modifier, and 3 to 7 wt % of the aqueous antibacterial composition.

The deionized water is added to prevent gelation from occurring during dispersion while allowing each composition component to be sufficiently dispersed. Each of the propylene glycol, the PMA solvent, the PM solvent, and the IPA is a sort of solvent for maximizing the reaction rate and workability of each composition component. The dispersing agent is added to allow the pigment which will be described later to be uniformly dispersed in the composition. The pigment is added to impart colors to the ink composition. The rheology modifier is added to impart flowability suitable for ensuring printing workability and storage stability. These composition components are materials that are widely used in the ink composition field and already known in the art, and thus a detailed description thereof will be omitted to avoid redundancy. The contents of the composition components have been specified as described above, but are not limited thereto and may vary depending on an object to be printed, the use environment of the to-be-printed object, the kind of prints and the like.

In the meantime, among the composition components whose material names are not defined in the composition, acryl polymer, as the dispersing agent, hydroxycarboxylic acid polymer, alkyleneoxide polymer chain, BYK-192 (BYK company, Germany) or the like can be used. Titanium dioxide, iron-aluminum titanate, iron oxide, carbon black, ultramarine blue, Dupont R-902 (Dupont Co., Ltd., USA) or the like can be used as the pigment. In addition, as the rheology modifier, silica, urea, urethane solution, RM-825 (Rohm and Haas Company, USA) or the like can be used, but it is also a material that is already known in the art, and thus is not limited to the above-mentioned kinds of materials. Various kinds of materials already known in the art can be used as the dispersing agent, the pigment and the rheology modifier.

The aqueous antibacterial composition is added to impart antibacterial properties to the ceramic printing ink composition, and the aqueous antibacterial composition as disclosed in Korean Patent No. 10-0999170 which was previously filed by the applicant and registered is used. More specifically, the aqueous antibacterial composition is prepared by adding and dispersing 45 to 55 parts by weight of silica nanotubes, 30 to 40 parts by weight of a wetting/dispersing agent, 30 to 40 parts by weight of a co-solvent, and 4 to 6 parts by weight of an antifoaming agent in 100 parts by weight of deionized water, and the silica nanotubes are used which contain 20000 to 100000 ppm of silver nanoparticles.

The silica nanotubes are silver nanoparticle-containing silica nanotubes having a high dispersion force as disclosed in Korean Patent No. 10-1010677 which was previously filed by the applicant and registered. Nanoparticles are contained in the silica nanotubes including fine pores having a size of 30 to 50 nm. The overall length of the silica nanotubes is set at a level on the order of 1 to 30 μm, and the silica nanotubes are excellent in dispersion force since a coagulation phenomenon or the like does not occur in any kind of water-soluble solvent. Meanwhile, the content of the silver nanoparticles contained in the silica nanotubes is preferably 20,000 to 100,000 ppm. If the content of the silver nanoparticles is less than 20,000 ppm, the antibacterial activities may not be sufficiently expressed. On the contrary, if the content of the silver nanoparticles exceeds 100,000 ppm, a problem may occur in that the manufacturing cost of the silica nanotubes is increased without a significant increase in the antibacterial performance, leading to economic inefficiency. In the meantime, the silica nanotubes are contained in an amount of 45 to 55 parts by weight in 100 parts by weight of deionized water. If the content of the silica nanotubes in the deionized water is less than the lower limit of the above-specified range, the antibacterial property may be degraded. On the contrary, if the content of the silica nanotubes in the deionized water exceeds the upper limit of the above-specified range, inconvenience in use may be incurred by caking caused by agglomeration of the aqueous antibacterial composition due to the excessive content of the silica nanotubes.

The wetting/dispersing agent is an additive having both wetting and dispersing functions. The wetting/dispersing agent acts to facilitate the dispersion of the silica nanotubes in the aqueous-based composition and inhibit the occurrence of a re-agglomeration phenomenon. In other words, the wetting/dispersing agent has a surface-active structure in which one molecule contains both a polar hydrophilic group and a non-polar hydrophobic group, and serves to reduce the interfacial tension between the surfaces of the silica nanotubes and the resin solution to thereby increase a diffusion force, resulting in an acceleration of wetting and thus an increase in the dispersion force of the aqueous antibacterial composition. In addition, preferably, the wetting/dispersing agent is contained in an amount of 30 to 40 parts by weight in 100 parts by weight of deionized water. If the content of the wetting/dispersing agent is less than 30 parts by weight, the dispersibility of the silica nanotubes may be deteriorated. Contrarily, if the content of the wetting/dispersing agent exceeds 40 parts by weight, a change in the physical properties of the aqueous-based composition may be caused without a remarkable improvement in the dispersibility of the silica nanotubes, leading to economic inefficiency. In the meantime, the wetting/dispersing agent that can be used in the present invention is preferably one or more selected from the group consisting of an aryl type, a polyester type, a polyether type, and an acryl type, which have a pigment affinity group. More specifically, for example, the wetting/dispersing agent that can be used in the present invention is preferably one or more selected from among DISPERBYK-190, 191, 192, 194, 2015, 2090, and 2091 (BYK Chemie GmbH, Germany).

Besides, preferably, the aqueous antibacterial composition according to the present invention additionally contains the co-solvent so as to impart wettability to the silica nanotubes and adjust the balance of the solvent. The co-solvent acts to improve wettability to the silica nanotubes and increase a boiling point by being mixed with water at a high boiling point to thereby prevent evaporation of the solvent, i.e., adjust the balance of the solvent. In addition, the co-solvent is preferably contained in an amount of 30 to 40 parts by weight in 100 parts by weight of deionized water. If the content of the co-solvent is less than 30 parts by weight, wettability may not be properly imparted to the silica nanotubes. Contrarily, if the content of the co-solvent exceeds 40 parts by weight, the balance of the solvent may not be sufficiently adjusted and a problem may be occur in workability of an aqueous paint due to the excessive content of the co-solvent. More specifically, for example, the co-solvent that can be used in the present invention is preferably one or more selected from the group consisting of butyl glycol, ethyl glycol, propylene glycol, butyl cellosolve, isopropyl alcohol, and propylene glycol methyl ether.

Further, the aqueous antibacterial composition according to the present invention additionally contains the antifoaming agent so as to suppress the generation of foams and the like when mixed in the aqueous-based composition. In the present invention, the antifoaming agent acts to remove air bubbles generated in the aqueous-based composition. In addition, the antifoaming agent is preferably contained in an amount of 4 to 6 parts by weight in 100 parts by weight of deionized water. If the content of the antifoaming agent is less than 4 parts by weight, air bubbles generated when mixed in the aqueous-based composition may not be sufficiently removed. Contrarily, if the content of the antifoaming agent exceeds 6 parts by weight, a change in other physical properties of the aqueous-based composition may be rather caused without a remarkable improvement in removal effects of air bubbles generated in the aqueous-based composition.

The antifoaming agent that can be used in the present invention is preferably a polysiloxane-based compound. More specifically, for example, the antifoaming agent is preferably BYK-024 (BYK Chemie GmbH, Germany).

Therefore, the ceramic printing ink composition according to the present invention can possess an antibacterial function by virtue of the above composition. In a process of printing a pattern using the ceramic printing ink composition, the pattern is printed between or on ceramic coating layers by pad, screen or stamp printing. More specifically, ceramic coating (sol-gel) layers (1-coat, 2-coat, 3-coat, etc.) are formed and set-to-touch, after which the ceramic printing ink composition is coated on the coating layer and heated and cured simultaneously with the coating layers. Thus, bonding and adhesive strength of the ceramic printing ink composition is enhanced to enable pattern printing to be more stably and easily performed on the ceramic coating layer. Herein, the ceramic coating (sol-gel) layers can use various ceramic coating layers that are already known in the art. For example, the ceramic coating (sol-gel) layers can use various ceramic coating layers which are disclosed in Korean Patent Nos. 10-1104680 and 10-1510444 owned by the applicant, but not limited thereto and may various ceramic coating layers that are already known in the art. Further, in the case where the ceramic coating layers are coated with them divided into the primer coat and the top coat, the primer coating may be implemented as a colored or transparent coating and the top coating may be implemented as a transparent coating.

Hereinafter, the present invention will be described in more detail by way of examples. It should be appreciated that the scope of the invention is not limited by only these examples.

1. Preparation of Ceramic Printing Ink Composition

Example 1

A ceramic printing ink composition was prepared by mixing 10 wt % of deionized water, 4 wt % of propylene glycol, 0.5 wt % of PMA solvent, 0.4 wt % of PM solvent, 2 wt % of IPA, 0.1 wt % of a dispersing agent (BYK-192), 15 wt % of a pigment (Dupont R-902), 65 wt % of a rheology modifier (RM-825), and 3 wt % of the aqueous antibacterial composition.

In this case, the aqueous antibacterial composition was prepared by adding and dispersing 45 parts by weight of silica nanotubes, 30 parts by weight of a wetting/dispersing agent (DISPERBYK-190), 30 parts by weight of a co-solvent (Butyl Glycol), and 4 parts by weight of an antifoaming agent (BYK-024) in 100 parts by weight of deionized water, and the silica nanotubes were used which contain 20,000 ppm of silver nanoparticles, are formed with fine pores having a size of 30 nm, and have an overall length of 1 μm.

Example 2

A ceramic printing ink composition was prepared by mixing 20 wt % of deionized water, 8 wt % of propylene glycol, 3 wt % of PMA solvent, 3 wt % of PM solvent, 4 wt % of IPA, 1 wt % of a dispersing agent (BYK-192), 31 wt % of a pigment (Dupont R-902), 25 wt % of a rheology modifier (RM-825), and 5 wt % of the aqueous antibacterial composition.

In this case, the aqueous antibacterial composition was prepared by adding and dispersing 50 parts by weight of silica nanotubes, 35 parts by weight of a wetting/dispersing agent (DISPERBYK-190), 35 parts by weight of a co-solvent (Butyl Glycol), and 5 parts by weight of an antifoaming agent (BYK-024) in 100 parts by weight of deionized water, and the silica nanotubes were used which contain 50,000 ppm of silver nanoparticles, are formed with fine pores having a size of 40 nm, and have an overall length of 15 μm.

Example 3

A ceramic printing ink composition was prepared by mixing 25 wt % of deionized water, 13 wt % of propylene glycol, 4 wt % of PMA solvent, 4 wt % of PM solvent, 5 wt % of IPA, 2 wt % of a dispersing agent (BYK-192), 35 wt % of a pigment (Dupont R-902), 5 wt % of a rheology modifier (RM-825), and 7 wt % of the aqueous antibacterial composition.

In this case, the aqueous antibacterial composition was prepared by adding and dispersing 55 parts by weight of silica nanotubes, 40 parts by weight of a wetting/dispersing agent (DISPERBYK-190), 40 parts by weight of a co-solvent (Butyl Glycol), and 6 parts by weight of an antifoaming agent (BYK-024) in 100 parts by weight of deionized water, and the silica nanotubes were used which contain 100,000 ppm of silver nanoparticles, are formed with fine pores having a size of 50 nm, and have an overall length of 30 μm.

Comparative Example 1

A ceramic printing ink composition in Comparative Example 1 was prepared in the same manner as in Example 1 except that the aqueous antibacterial composition is not added thereto.

Comparative Example 2

A ceramic printing ink composition in Comparative Example 2 was prepared in the same manner as in Example 2 except that the aqueous antibacterial composition is not added thereto.

Comparative Example 3

A ceramic printing ink composition in Comparative Example 3 was prepared in the same manner as in Example 3 except that the aqueous antibacterial composition is not added thereto.

2. Evaluation of Ceramic Printing Ink Composition (1) Evaluation of Antibacterial Property An antibacterial activity test was performed on *Escherichia coli* and *Staphylococcus aureus* based on JIS Z 2801: 2006 (antibacterial products, antibacterial property test method, antibacterial effect), and the test results are shown in Table 1 below. *Escherichia coli* ATCC 8739 and *Staphylococcus aureus* ATCC 6538p were respectively used as test strains. In addition, an antibacterial activity value (R) was calculated by the following equation:

Antibacterial activity value $(R)=[\log(B/A)/\log(C/A)]=[\log(B/C)]$

In the above equation,

A: an average value of the number of viable cells immediately after a non-treated specimen B: an average value of the number of viable cells after 24 hours of inoculation of a non-treated specimen C: an average value of the number of viable cells after 24 hours of inoculation of an antibacterial-treated specimen

TABLE 1

| Test Items | | Ex. 1 | Ex. 2 | Ex. 3 | Comp. Ex. 1 | Comp. Ex. 2 | Comp. Ex. 3 |
|---|---|---|---|---|---|---|---|
| Antibacterial test (*E. coli*) | Antibacterial activity value (R) | 6.1 log | 6.1 log | 6.2 log | Exhibiting no antibacterial function | | |
| Antibacterial test (*S. aureusi*) | Antibacterial activity value (R) | 3.3 log | 3.4 log | 3.5 log | Exhibiting no antibacterial function | | |

It can be seen from the above Table 1 that the ceramic printing ink compositions according to Examples of the present invention have an excellent antibacterial function.

(2) Evaluation of Wettability

A ceramic coating layer was formed on the surface of an object to be printed and was set-to-touch. Thereafter, the ink compositions prepared in Examples 1 to 3 and Comparative Examples 1 to 3 were stamp-printed on the ceramic coating layer, and heated and cured. Then, the water contact angles against the surfaces of the printed ink compositions were measured by a contact angle measurement method which includes the steps of: washing the surfaces of the printed ink compositions with a weak alkali detergent or a neutral detergent aqueous solution and a sponge; drying the washed surfaces; dropping water droplets onto the dried surfaces; and measuring the water contact angles against the surfaces of the printed ink compositions using a contact angle measurement device (SEO300A, Surface and Electro-Optics Co., Ltd, Korea). The results of the measurement of the water contact angles are shown in Table 2 below.

(3) Evaluation of Adhesion

A ceramic coating layer was formed on the surface of the to-be-printed object and was set-to-touch. Thereafter, the ink compositions prepared in Examples 1 to 3 and Comparative Examples 1 to 3 were stamp-printed on the ceramic coating layer, and heated and cured. Then, the surfaces of the printed ink composition layers were cross-cut to 1 mm×1 mm (10×10 ea) in size, and immersed in boiled water for 5 minutes and then dried. Then, the cross-cut printed ink composition layers were detached with a Scotch tape, and then an evaluation was made on the detached printed ink composition layers in terms of adhesion. The results of the evaluation of the adhesion are shown in Table 2 below.

TABLE 2

| Test Items | | Ex. 1 | Ex. 2 | Ex. 3 | Comp. Ex. 1 | Comp. Ex. 2 | Comp. Ex. 3 |
|---|---|---|---|---|---|---|---|
| Wettability | Water contact angle | 20° | 22° | 21° | 82° | 80° | 81° |
| Adhesion | Adhesion rate | 100% | 100% | 100% | 20% (peeling rate of more than 80%) | 20% (peeling rate of more than 80%) | 20% (peeling rate of more than 80%) |

It can be seen from the above Table 2 that the ceramic printing ink compositions according to Examples of the present invention have an excellent wettability and adhesion against the ceramic surface so that pattern printing can be stably and easily performed on the ceramic coating layer.

As described above, while the preferred embodiments of a ceramic printing ink composition having an antibacterial function according to the present invention has been described and illustrated in connection with specific exemplary embodiments with reference to the accompanying drawings and excellence of the composition of the present invention has been confirmed, it will be readily appreciated by those skilled in the art that it is merely illustrative of the preferred embodiments of the present invention and various modifications and changes can be made to the present invention within the technical spirit and scope of the present invention defined in the claims.

Best Mode

In a best mode for carrying out the invention, a ceramic printing ink composition having an antibacterial function of the present invention comprises an aqueous antibacterial composition. More specifically, the ceramic printing ink composition having an antibacterial function may preferably comprise 10 to 25 wt % of deionized water, 4 to 13 wt % of propylene glycol, 0.5 to 4 wt % of PMA solvent, 0.4 to 4 wt % of PM solvent, 2 to 5 wt % of IPA, 0.1 to 2 wt % of a dispersing agent, 15 to 35 wt % of a pigment, 5 to 65 wt % of a rheology modifier, and 3 to 7 wt % of the aqueous antibacterial composition.

In the meantime, the aqueous antibacterial composition may preferably be prepared by adding and dispersing 45 to 55 parts by weight of silica nanotubes, 30 to 40 parts by weight of a wetting/dispersing agent, 30 to 40 parts by weight of a co-solvent, and 4 to 6 parts by weight of an antifoaming agent in 100 parts by weight of deionized water, and the silica nanotubes may preferably contain 20000 to 100000 ppm of silver nanoparticles. In addition, the silica nanotubes may preferably include fine pores having a size of 30 to 50 nm, and have an overall length of 1 to 30 μm.

Industrial Applicability

According to the present invention, a coating binder can be absorbed during a printing/drying/curing process to achieve a bonding strength of the ink itself and a firm bonding between the ink and the ceramic coating layer. In addition, the ceramic printing ink composition of the present invention possesses an antibacterial function by using the aqueous antibacterial composition such that the overall composition can have a good miscibility so as not to hinder the antibacterial function of the aqueous antibacterial composition. Further, the ceramic printing ink composition of the present invention can implement a good wettability with respect to the ceramic coating layer through the adjustment of the surface tension, and have flowability and drying property that are suitable for ensuring workability of pad, screen or stamp printing and storage stability. Moreover, the ceramic printing ink composition of the present invention can be printed on the ceramic coating layer, particularly a sol-gel nonstick coating layer, and can minimize the effect of the coating layer on a change in the physical properties at the printing site by ensuring good adhesion properties and selecting of the constituent components. Therefore, the ceramic printing ink composition according to the present invention is expected to be widely used in industrial applications.

The invention claimed is:

1. A ceramic printing ink composition having an antibacterial function, the composition comprising an aqueous antibacterial composition, wherein the composition comprises 10 to 25 wt % of deionized water, 4 to 13 wt % of propylene glycol, 0.5 to 4 wt % of PMA solvent, 0.4 to 4 wt % of PM solvent, 2 to 5 wt % of IPA, 0.1 to 2 wt % of a dispersing agent, 15 to 35 wt % of a pigment, 5 to 65 wt % of a rheology modifier, and 3 to 7 wt % of the aqueous antibacterial composition.

2. The ceramic printing ink composition according to claim 1, wherein the aqueous antibacterial composition is prepared by adding and dispersing 45 to 55 parts by weight of silica nanotubes, 30 to 40 parts by weight of a wetting/dispersing agent, 30 to 40 parts by weight of a co-solvent, and 4 to 6 parts by weight of an antifoaming agent in 100 parts by weight of deionized water, and wherein the silica nanotubes contain 20,000 to 100,000 ppm of silver nanoparticles.

3. The ceramic printing ink composition according to claim 2, wherein the silica nanotubes include fine pores having a size of 30 to 50 nm, and have an overall length of 1 to 30 μm.

* * * * *